United States Patent [19]
Krzysik et al.

[11] Patent Number: 5,665,426
[45] Date of Patent: Sep. 9, 1997

[54] SOFT TREATED TISSUE

[75] Inventors: Duane Gerard Krzysik, Appleton; Lee Patrick Garvey, Little Chute; Cynthia Watts Henderson, Neenah; Michael Chauncey Tuck, Appleton, all of Wis.

[73] Assignee: Kimberly-Clark Corporation, Nennah, Wis.

[21] Appl. No.: 384,170

[22] Filed: Feb. 6, 1995

[51] Int. Cl.⁶ .................................................. B05D 1/00
[52] U.S. Cl. .................. 427/211; 427/209; 427/210; 427/278; 427/288; 427/382; 427/391
[58] Field of Search .................................. 427/209, 210, 427/211, 278, 288, 382, 391

[56] References Cited

U.S. PATENT DOCUMENTS

| | | | |
|---|---|---|---|
| 2,999,265 | 9/1961 | Duane et al. | 15/506 |
| 3,150,049 | 9/1964 | Emory | 167/90 |
| 3,264,188 | 8/1966 | Gresham | 167/84 |
| 3,619,280 | 11/1971 | Scheuer | 117/154 |
| 3,896,807 | 7/1975 | Buchalter | 128/261 |
| 3,950,578 | 4/1976 | Laumann | 427/378 |
| 4,112,167 | 9/1978 | Dake et al. | 428/154 |
| 4,481,243 | 11/1984 | Allen | 428/154 |
| 4,513,051 | 4/1985 | Lavash | 428/212 |
| 4,550,035 | 10/1985 | Smith | 427/398.1 |
| 4,572,915 | 2/1986 | Crooks | 514/458 |
| 4,659,573 | 4/1987 | Frischling et al. | 424/63 |
| 4,735,935 | 4/1988 | McAnalley | 514/53 |
| 4,806,418 | 2/1989 | Sigl | 428/284 |
| 4,816,320 | 3/1989 | St. Cyr | 428/198 |
| 4,839,162 | 6/1989 | Komori et al. | 424/63 |
| 4,891,227 | 1/1990 | Thaman et al. | 424/443 |
| 4,891,228 | 1/1990 | Thaman et al. | 424/443 |

(List continued on next page.)

FOREIGN PATENT DOCUMENTS

| | | |
|---|---|---|
| 508516 | 5/1978 | Australia . |
| 564042 | 9/1983 | Australia . |
| 566215 | 10/1987 | Australia . |
| 579458 | 12/1987 | Australia . |
| 38925/89 | 7/1989 | Australia . |
| 620748 | 12/1990 | Australia . |
| 84845/91 | 9/1991 | Australia . |
| 638399 | 6/1993 | Australia . |
| 640529 | 8/1993 | Australia . |
| 644499 | 9/1993 | Australia . |
| 644457 | 12/1993 | Australia . |
| 0032793 | 3/1984 | European Pat. Off. . |
| 0165696 | 12/1985 | European Pat. Off. . |
| 0191128 | 8/1986 | European Pat. Off. . |
| 0257824 | 3/1988 | European Pat. Off. . |
| 0524892 | 1/1993 | European Pat. Off. ......... A61K 7/48 |
| 2538238 | 8/1987 | France . |
| 485 947 | 10/1929 | Germany . |
| 490 263 | 1/1930 | Germany . |
| 2746098 | 4/1979 | Germany . |
| 8704537 | 9/1987 | Germany . |
| 3720232 | 7/1988 | Germany . |
| 3924898 | 1/1991 | Germany . |
| 5916816 | 2/1984 | Japan . |
| 62-236516 | 1/1987 | Japan . |
| 63-275311 | 11/1988 | Japan . |
| 274694 | 1/1990 | Japan . |
| 2182999 | 11/1990 | Japan . |
| 3182218 | 5/1991 | Japan . |
| 415021 | 3/1992 | Japan . |
| 520093 | 9/1993 | Japan . |
| 253 918 | 11/1948 | Switzerland . |
| 1591294 | 6/1981 | United Kingdom . |
| 9305752 | 4/1993 | WIPO . |
| 9316678 | 9/1993 | WIPO . |
| 9402674 | 2/1994 | WIPO . |

*Primary Examiner*—James J. Bell
*Attorney, Agent, or Firm*—Gregory E. Croft

[57] ABSTRACT

A soft tissue product is disclosed having uniformly distributed surface deposits of a solidified composition having a melting point of from about 30° C. to about 70° C. The solidified composition is applied to the outer surfaces of the tissue product in melted form, preferably by rotogravure printing. The solidified composition contains an oil, a wax, and preferably a fatty alcohol.

15 Claims, 10 Drawing Sheets

U.S. PATENT DOCUMENTS

| | | | |
|---|---|---|---|
| 4,917,890 | 4/1990 | McAnalley | 424/195.1 |
| 4,950,545 | 8/1990 | Walter et al. | 428/446 |
| 5,085,856 | 2/1992 | Durphy et al. | 424/64 |
| 5,179,128 | 1/1993 | Lyle et al. | 252/165 |
| 5,281,306 | 1/1994 | Kakiuchi et al. | 162/158 |
| 5,362,500 | 11/1994 | Mazurek et al. | 426/5 |
| 5,389,204 | 2/1995 | Ampulski | 162/135 |
| 5,525,345 | 6/1996 | Warner et al. | 424/402 |

SOFT TREATED TISSUE

BACKGROUND OF THE INVENTION

Absorbent tissue products such as facial tissue and bath tissue have been used to absorb body fluids and leave the skin dry. Absorbent tissues, in addition to absorbing fluids, however, have also abraded the skin. In particular, during frequent nose-blowing, the skin can become so abraded as to appear red and be sore to the touch. To reduce skin abrasion, tissue additive formulations can be applied to the tissue such that, in use, the additive formulation either provides lubricity causing the tissue to glide across the surface of the skin, or leaves the tissue and is deposited on the skin.

To date, these formulations have been liquids or semi solids at room temperature to enable them to be easily deposited onto the tissue. A high amount of these liquids is required to be deposited on the tissue to deliver the benefit of reduced skin irritation and redness because these liquids absorb into the tissue, leaving less on the surface to provide the benefit.

Thus, there is a need for a formulation that can be applied to a tissue which will remain readily available for transfer to the user's skin to reduce skin irritation and redness in an efficient cost-effective manner.

SUMMARY OF THE INVENTION

It has now been discovered that a superior soft tissue product can be made by applying, on the surface(s) of the tissue, large numbers of individual deposits of a melted moisturizing/protective composition comprising a wax and an oil, and thereafter resolidifying the composition to form a distribution, preferably a uniform distribution, of solid deposits on the surface(s) of the tissue. Because the composition is a solid at room temperature and rapidly solidifies after deposition, it has less tendency to penetrate and migrate into the sheet. Compared to tissues treated with liquid formulations, this leaves a greater percentage of the added composition on the surface of the tissue where it can contact and transfer to the user's skin to provide a benefit. Furthermore, a lower add-on amount can be used to deliver the same benefit at lower cost because of the efficient placement of the composition substantially at the surface of the product.

Hence, in one aspect the invention resides in a tissue product having one or more plies, wherein one or both of the outer surfaces of the product have uniformly distributed solidified deposits of a composition comprising from about 30 to about 90 weight percent oil, and from about 10 to about 40 weight percent wax, preferably also containing from about 5 to about 40 weight percent fatty alcohol, said composition having a melting point of from about 30° C. to about 70° C., more specifically from about 40° C. to about 60° C. For purposes herein, "melting point" is the temperature at which the majority of the melting occurs, it being recognized that melting actually occurs over a range of temperatures.

In another aspect, the invention resides in a method of making a soft tissue product comprising: (a) heating a composition comprising an oil, wax, and preferably a fatty alcohol, to a temperature above the melting point of the composition, causing the composition to melt, said composition having a melting point of from about 30° C. to about 70° C.; (b) uniformly applying the melted composition to one or both surfaces of a tissue web in spaced-apart deposits; and (c) resolidifying the deposits of the melted composition. Resolidification of the deposits can occur almost instantaneously, without the need for external cooling means such as chill rolls, if the composition is heated to a temperature only slightly above or at the melting point of the composition. However, external cooling means such as chill rolls, either before or after the application of the melt, can be used if desired to accelerate resolidification. Such instantaneous resolidification tends to impede penetration of the composition into the tissue and retain it on the surface of the tissue, which is advantageous. For example, the temperature of the melted composition can advantageously be above the melting point about 10° C. or less, more specifically about 5° C. or less, and still more specifically about 2° C. or less. As the temperature of the melted composition approaches the melting point, the viscosity of the melted composition generally increases, which further enhances the tendency of the melted composition to be retained on the surface.

The amount of oil in the composition can be from about 30 to about 90 weight percent, more specifically from about 40 to about 70 weight percent, and still more specifically from about 45 to about 60 weight percent. Suitable oils include, but are not limited to, the following classes of oils: petroleum or mineral oils, such as mineral oil and petrolatum; animal oils, such as mink oil and lanolin oil; plant oils, such as aloe extract, sunflower oil and avocado oil; and silicone oils, such as dimethicone and alkyl methyl silicones.

The amount of wax in the composition can be from about 10 to about 40 weight percent, more specifically from about 10 to about 30 weight percent, and still more specifically from about 15 to about 25 weight percent. Suitable waxes include, but are not limited to the following classes: natural waxes, such as beeswax and carnauba wax; petroleum waxes, such as paraffin and ceresine wax; silicone waxes, such as alkyl methyl siloxanes; or synthetic waxes, such as synthetic beeswax and synthetic sperm wax.

The amount of fatty alcohol in the composition, if present, can be from about 5 to about 40 weight percent, more specifically from about 10 to about 30 weight percent, and still more specifically from about 15 to about 25 weight percent. Suitable fatty alcohols include alcohols having a carbon chain length of $C_{14}$–$C_{30}$, including cetyl alcohol, stearyl alcohol, behenyl alcohol, and dodecyl alcohol.

In order to better enhance the benefits to consumers, additional ingredients can be used. The classes of ingredients and their corresponding benefits include, without limitation, $C_{10}$ or greater fatty alcohols (lubricity, body, opacity); fatty esters (lubricity, feel modification); vitamins (topical medicinal benefits); dimethicone (skin protection); powders (lubricity, oil absorption, skin protection); preservatives and antioxidants (product integrity); ethoxylated fatty alcohols; (wetability, process aids); fragrance (consumer appeal); lanolin derivatives (skin moisturization), colorants, optical brighteners, sunscreens, alpha hydroxy acids, natural herbal extracts, and the like.

The total tissue add-on amount of the composition can be from about 1 to about 40 weight percent, more specifically from about 5 to about 25 weight percent, and still more specifically from about 10 to about 15 weight percent, based on the weight of the tissue. The add-on amount will depend upon the desired effect of the composition on the product attributes and the specific composition. A preferred method to uniformly apply the heated composition to the surface of the tissue web is rotogravure printing, either direct or indirect (offset), because it is the most exact printing process and offers maximum control of the composition distribution and transfer rate. However, other printing methods, such as flexographic printing, can also be used.

The surface area coverage of the composition is preferably uniform over substantially all of the tissue surface, but only partially covers the surface(s) of the tissue product. This is achieved by a large number of small spaced-apart deposits which, when viewed by the naked eye, appear to cover the entire surface, but in fact do not. The actual surface area coverage of the deposits can be from about 30 to about 99 percent, more specifically from about 50 to about 80 percent. ("Surface area" is the area of a simple plan view of the tissue, not taking into account the three-dimensional topography of the tissue which would otherwise increase the surface area value for any given tissue sample). By providing a large number of very small deposits, the penetration of the composition can be more easily controlled to substantially remain on or near the surface of the tissue. Gravure printing is ideally suited to such an application by providing, for example, from about 10 to about 1000 deposits per lineal inch of surface, or from about 100 to about 1,000,000 deposits per square inch. This encompasses several well known engraving techniques, such as mechanical engraving, acid-etch engraving, electronic engraving and ceramic laser engraving. A suitable electronic engraved example is about 250 deposits per lineal inch of surface, or about 62,500 deposits per square inch. By providing such a large number of small deposits, the uniformity of the deposit distribution is very high. The uniformity can be quantified by image analysis as will hereinafter be described and preferably can be characterized by a percent coefficient of variation of about 15 or less, more specifically about 10 or less, and still more specifically from about 5 to about 15. Because of the large number of small deposits applied to the surface of the tissue, the deposits more readily resolidify on the surface of the tissue where they is most effective in benefiting the user. As a consequence, a relatively low amount of the composition can be used to cover a large area.

In some embodiments, the products of this invention can be characterized by their hydrophobicity, which helps prevent "wet-through" to the user's hands during use. This property can be objectively measured by the Sink Time, which is described in U.S. Pat. No. 4,950,545 entitled "Multifunctional Facial Tissue" and issued Aug. 21, 1990 to Walter et al., which is herein incorporated by reference. The Sink Time can be about 30 seconds or greater, more specifically about 40 seconds or greater, still more specifically from about 50 to about 150 seconds or greater. These Sink Times can be dramatically increased by a factor of 3–5 times by heating the treated tissues of this invention to temperatures of from about 100° to about 150° F. Heat treated tissues can exhibit Sink Times of about 150 or greater.

The tissue product of this invention can be one-ply, two-ply, three-ply or more. In all cases, the composition is applied to the outer surface(s) of the product. The composition can be applied after the plies are brought together or prior to bringing the plies together. The individual plies can be layered or blended (homogeneous), creped or uncreped, throughdried or wet-pressed. Surprisingly, it had been found that blended tissue basesheets provide equivalent performance to layered basesheets, hence layering is unnecessary.

DETAILED DESCRIPTION OF THE DRAWING

Figure 1:
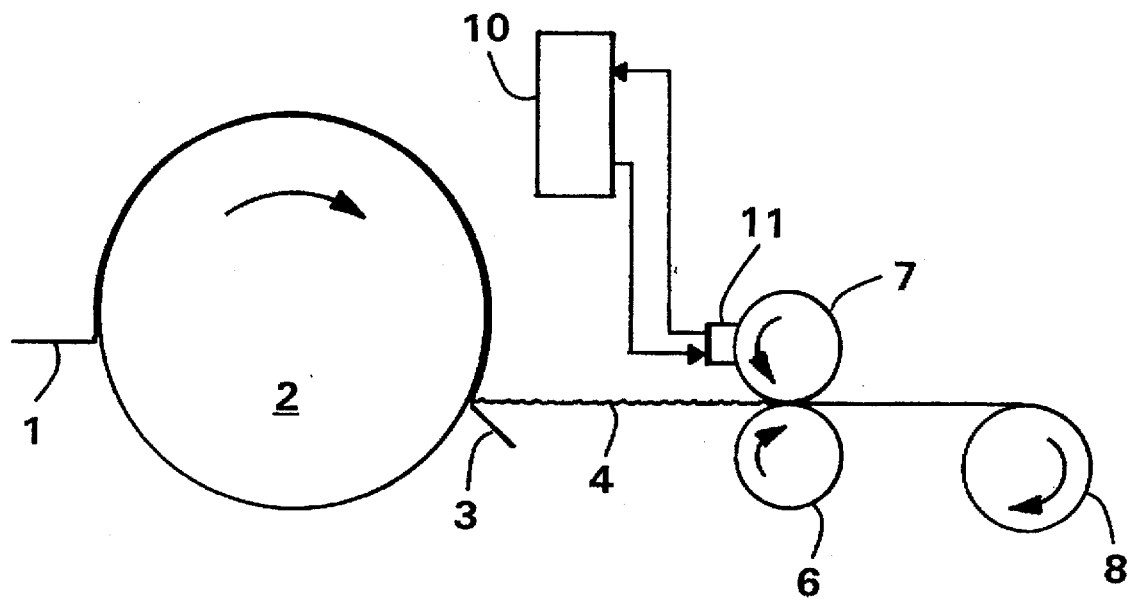
FIG. 1 is a schematic process flow diagram of a method of this invention in which the composition is applied to a creped tissue sheet during manufacturing using a heated rotogravure printer.

In the descriptions of the following figures, the same reference numerals will be used to depict the same items from figure to figure.

Referring to FIG. 1, one aspect of the invention will be described in greater detail. Shown is a tissue sheet 1 approaching a Yankee dryer 2 and being dislodged from the dryer with a creping blade 3. The dried creped tissue sheet 4 is passed to a heated rotogravure printing station comprising backing roll 6 and engraved roll 7, at which point the melted composition is applied to one surface of the tissue sheet. The treated tissue sheet is then wound into a roll 8 for subsequent converting operations.

During the printing operation, the melted composition to be applied to the tissue sheet is supplied by a heated supply tank 10 and pumped to the heated doctor application head 11 by a suitable metering pump. It is necessary to maintain constant temperature in the process. Accordingly, the melted composition is continually circulated between the supply tank and the application head while maintaining an adequate amount in the reservoir. The heated doctor applicator head supplies the melted composition to the engraved roll, the surface of which contains a plurality of small cells having a transfer volume necessary to achieve the desired effect. By way of example, a suitable engraved roll has a line screen of 250 lines per lineal inch and a volume of 5.0 billion cubic microns (BCM) per square inch of roll surface. Typical cell dimensions for this roll are 150 microns in length, 110 microns in width, and 30 microns in depth.

In operation the engraved roll is loaded to the backing roll to force the tissue web or sheet into contact with the engraved roll. The backing roll can be any material that meets the process requirements such as natural rubber, synthetic rubber or other compressible surfaces. Loading pressures can vary from approximately 5–50 pli (roll to roll interference) to a gravure roll/backing roll gap of 0.008" (no roll to roll contact).

Figure 2:
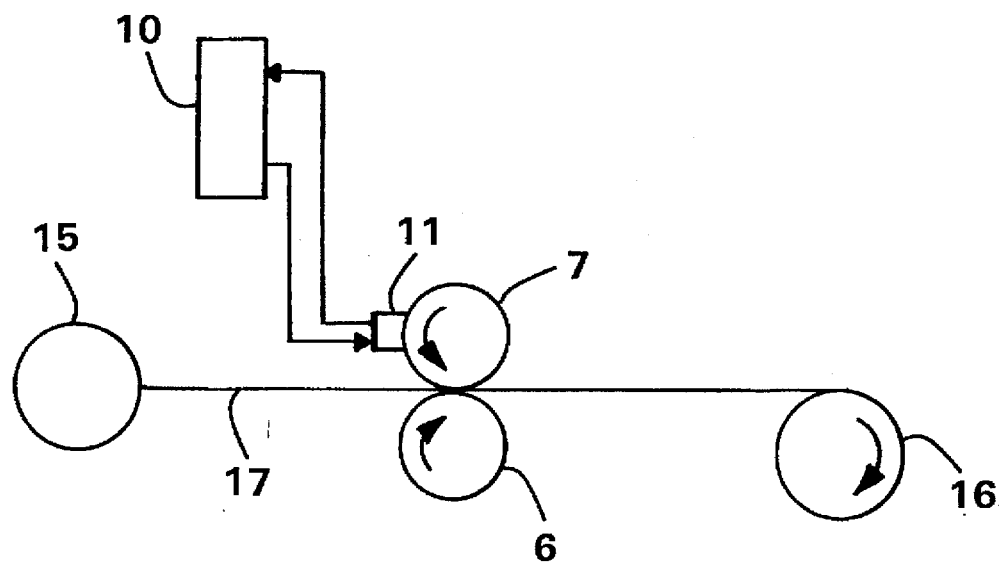
FIG. 2 is a schematic process flow diagram of a method of this invention similar to FIG. 1, in which the web to be treated is sourced from a parent roll.

FIG. 2 is similar to FIG. 1, differing only in that the tissue sheet to be printed with the melted composition is supplied from a parent roll 15. This is intended to depict off-line printing, in which the printing operation is carried out independently of the tissue sheet manufacturing process. The sheet 17 being printed with the melted composition can be a single ply or it can be multiple plies. The resulting sheet is then wound into a roll 16 for further converting operations.

Figure 3:
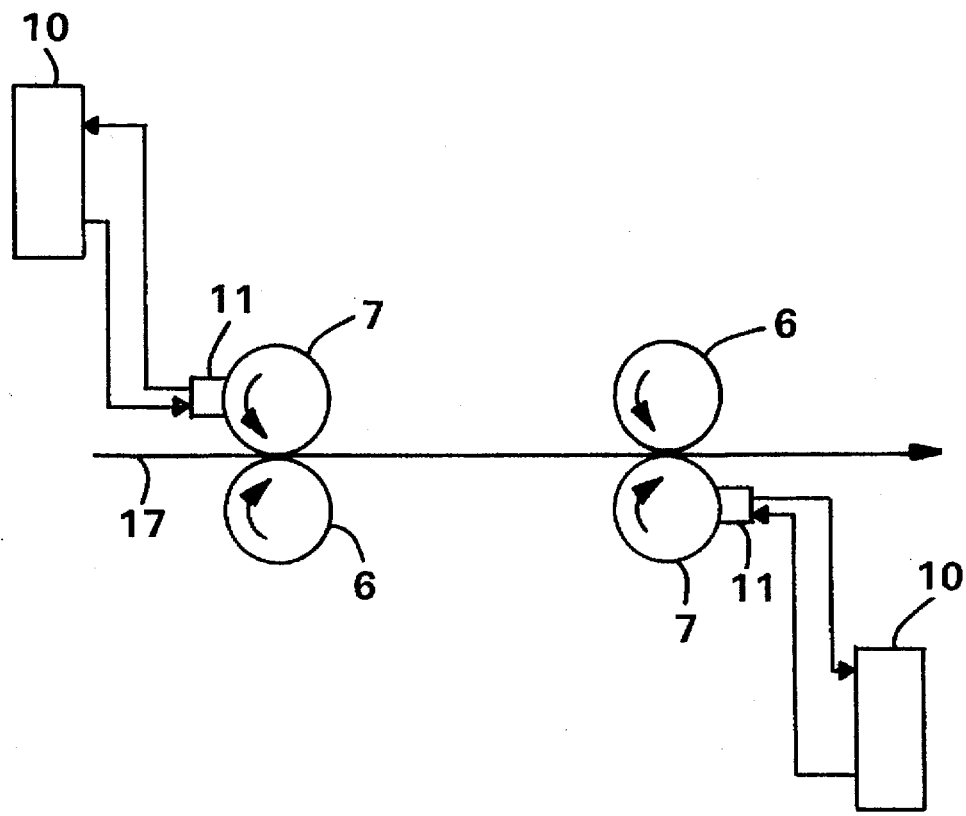
FIG. 3 is a schematic depiction of the heated rotogravure process in which the melted composition is applied to both sides of the tissue sheet.

FIG. 3 is similar to FIG. 2, but illustrates two-sided direct heated rotogravure printing of the sheet using two printing stations in sequence. Two-sided printing is desirable when the effect of adding the composition is desired on both sides of a single ply product or when the tissue product consists of two or more plies.

Figure 4:
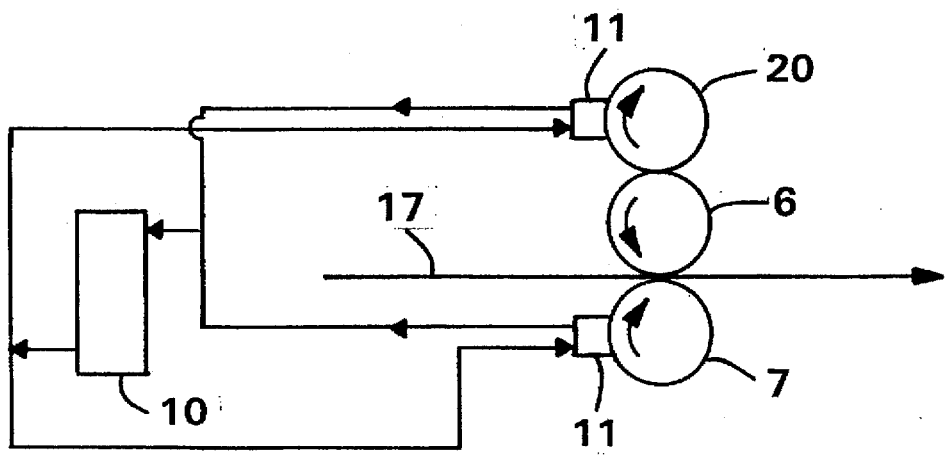
FIG. 4 is a further schematic depiction of a method of this invention in which both sides of the tissue product are printed with the melted composition using a combination of heated offset gravure printing and heated direct gravure printing.

FIG. 4 represents two-sided printing of the tissue sheet using an offset heated gravure printing method on one side of the sheet and a direct heated gravure printing method on the other side of the sheet. In this method, the engraved roll 7 and the backup roll 6 (now doubling as an offset applicator roll) can be the same as the rolls used for the previously described methods. However, the second engraved roll 20 requires different liquid delivery characteristics and thus is engraved slightly differently. For such rolls, for example, the direct engraving specifications can be 250 line screen, 5.0 BCM. Typical cell dimensions for such a roll can be 150 microns in length, 110 microns in width, and 30 microns in depth. The offset engraving specifications can be 250 line screen, 4.0 BCM, 140 microns in length, 110 microns in width, and 26 microns in depth.

Figure 5:
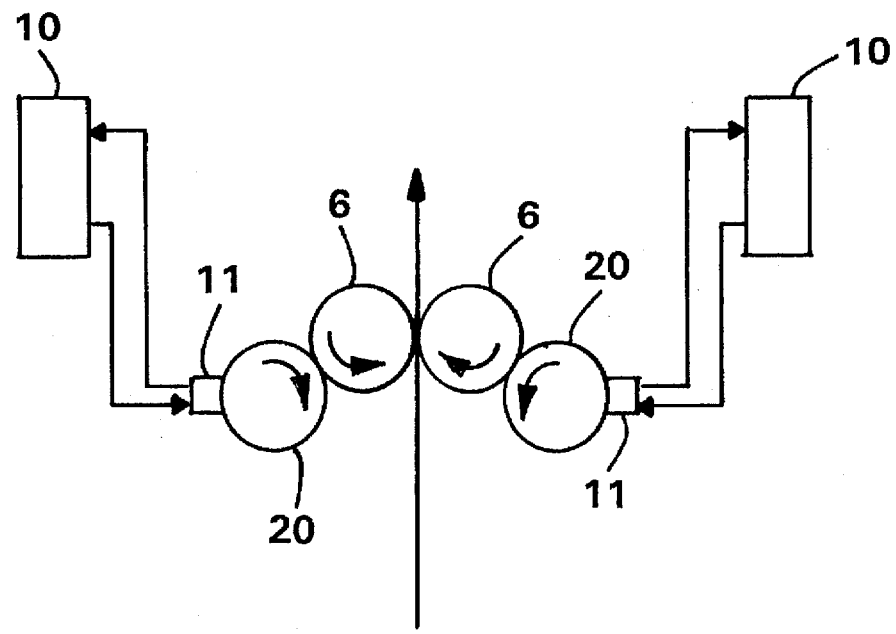
FIG. 5 is a further schematic depiction of a method of this invention in which both sides of a tissue sheet are simultaneously printed with the melted composition using heated offset gravure printing.

FIG. 5 represents a method of printing both sides of the sheet using simultaneous heated offset gravure printing.

Figure 6:
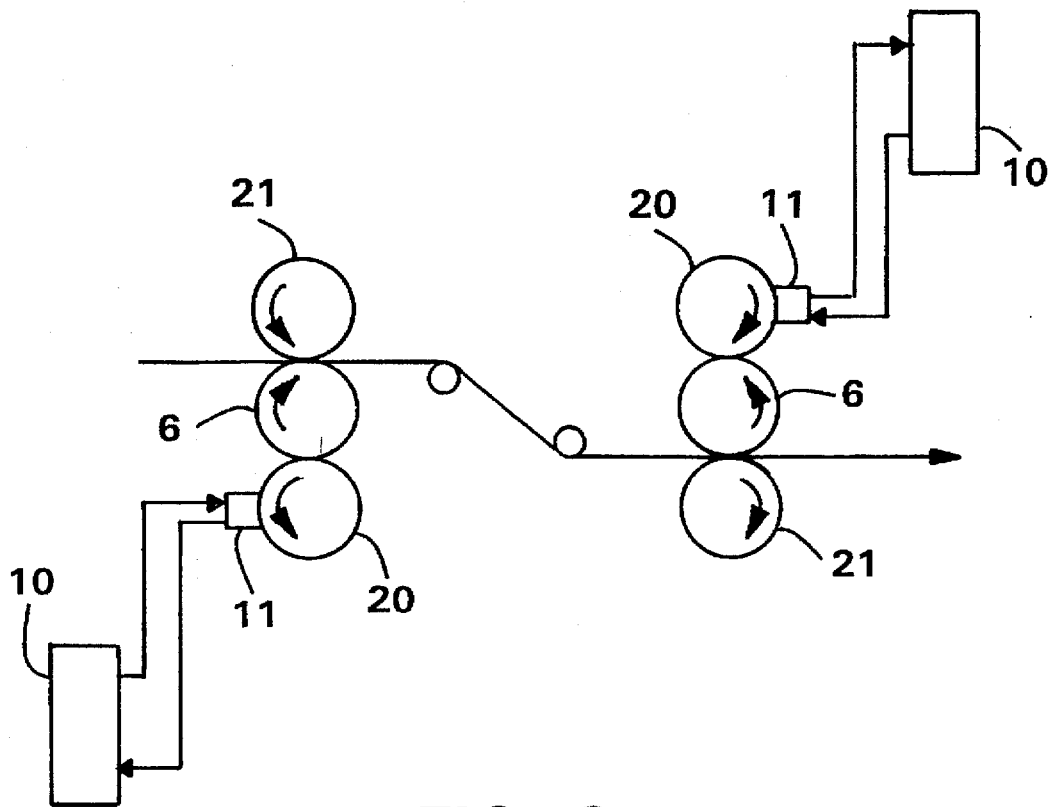
FIG. 6 is a further schematic depiction of a method of this invention in which both sides of the tissue sheet are consecutively printed with the melted composition using heated offset gravure printing.

FIG. 6 represents a method of printing both sides of the sheet in succession using two heated offset gravure printing stations. For each printing station, the addition of a backing roll 21 is necessary.

Figure 7A:
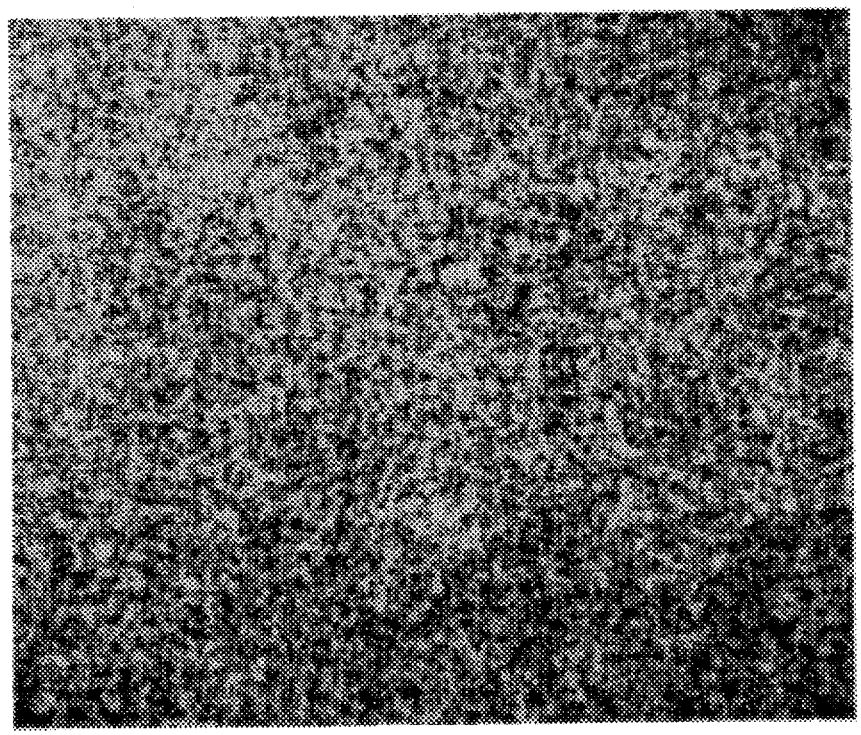
FIGS. 7A and 7B are photographs of the surfaces of an osmium tetroxide-stained tissue of this invention and that of a commercially-available lotion-treated tissue, respectively, illustrating the area coverage of the two compositions.
Figure 7B:
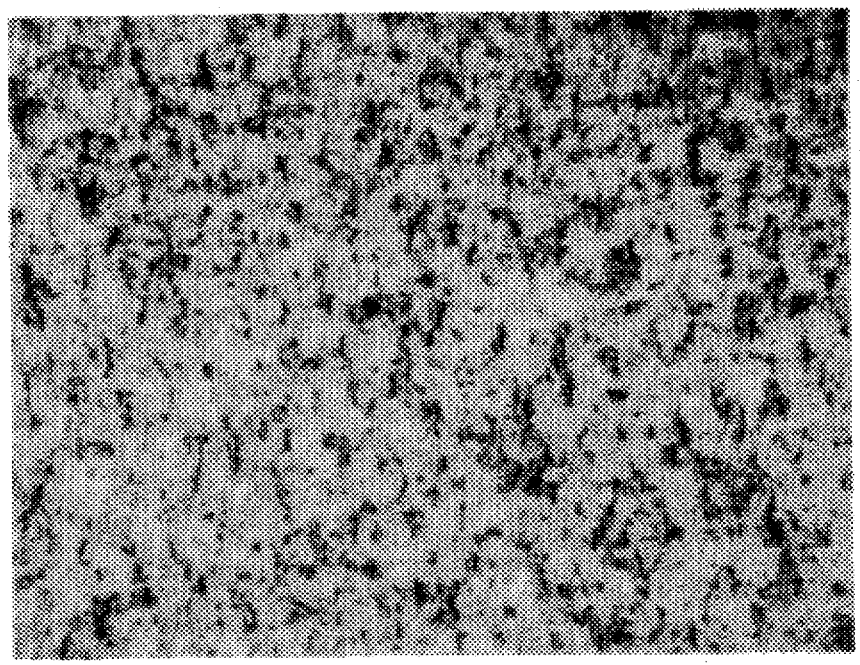
Figure 8A:
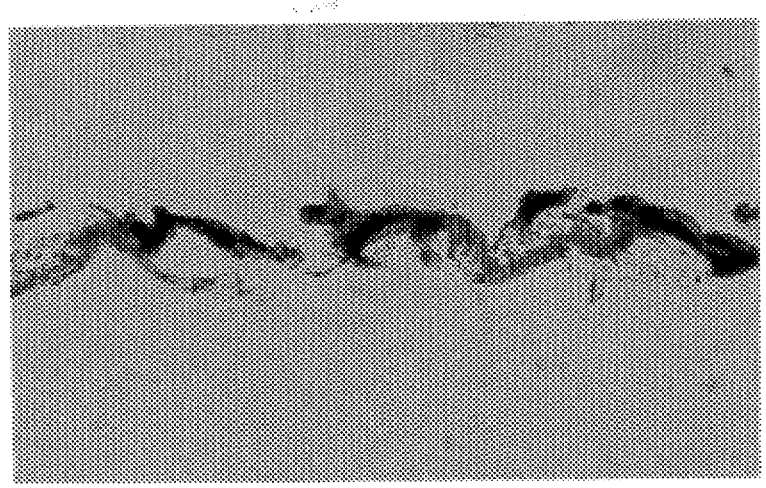
FIGS. 8A–F and 9A–F are cross-sectional photographs of two osmium tetroxide-stained tissues in accordance with this invention, illustrating the degree of penetration of the treatment compositions.
Figure 8B:
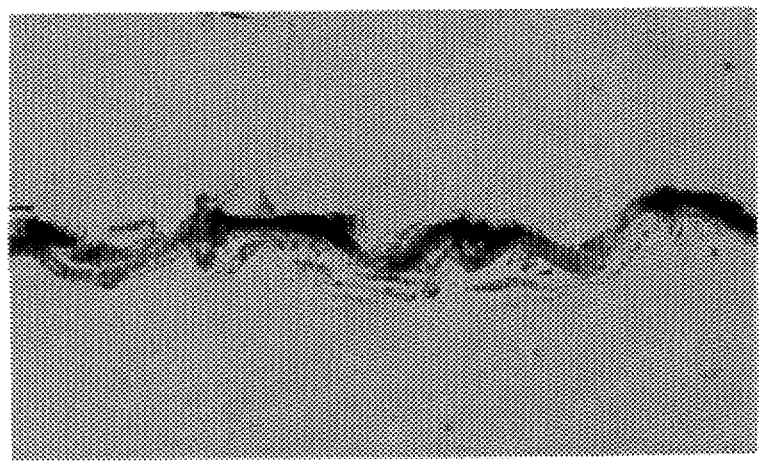
Figure 8C:
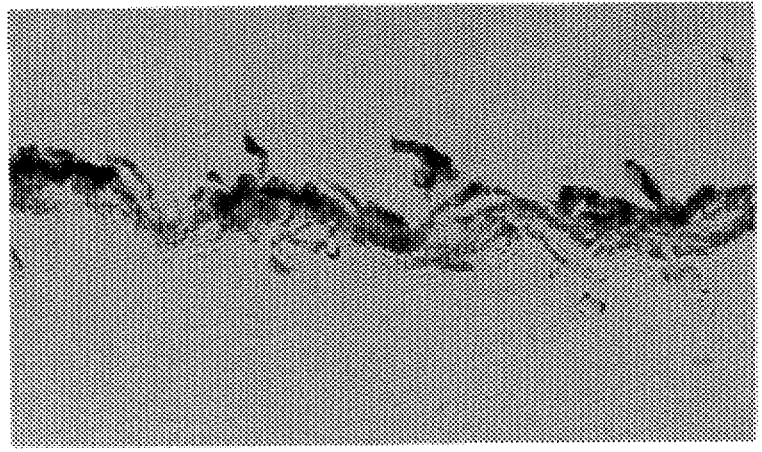
Figure 8D:
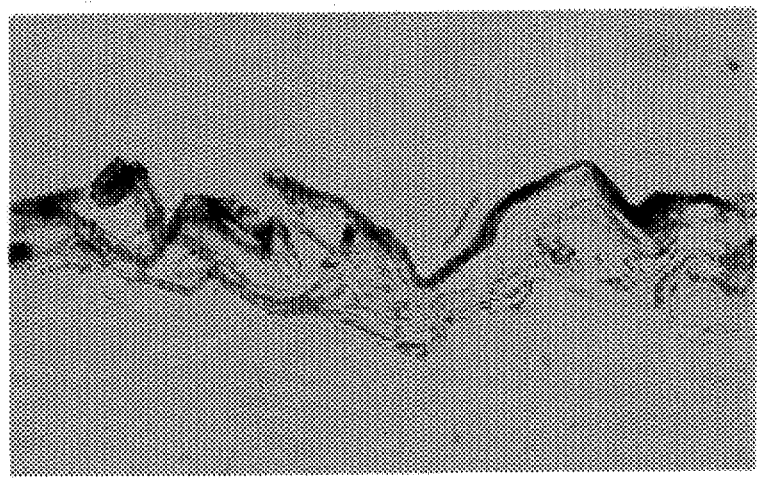
Figure 8E:
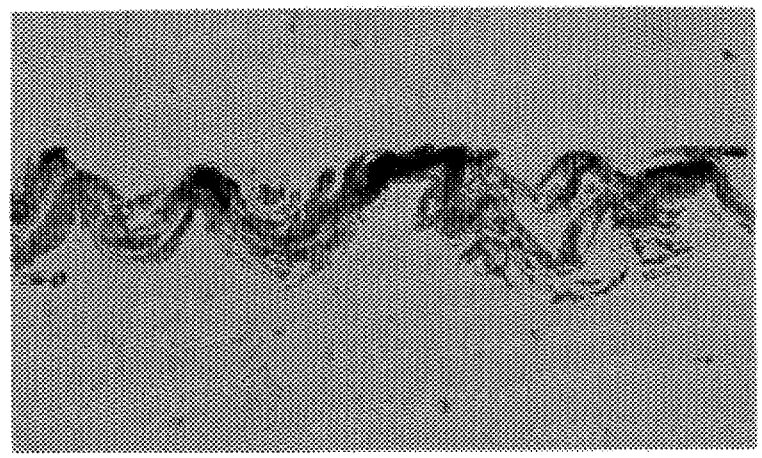
Figure 8F:
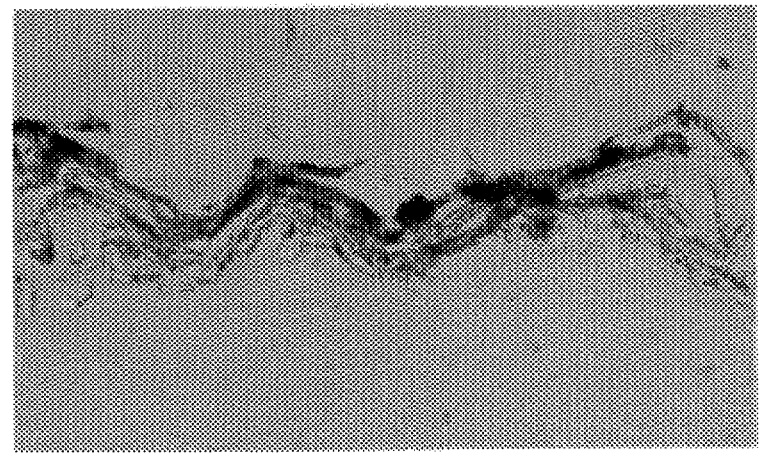
Figure 9A:
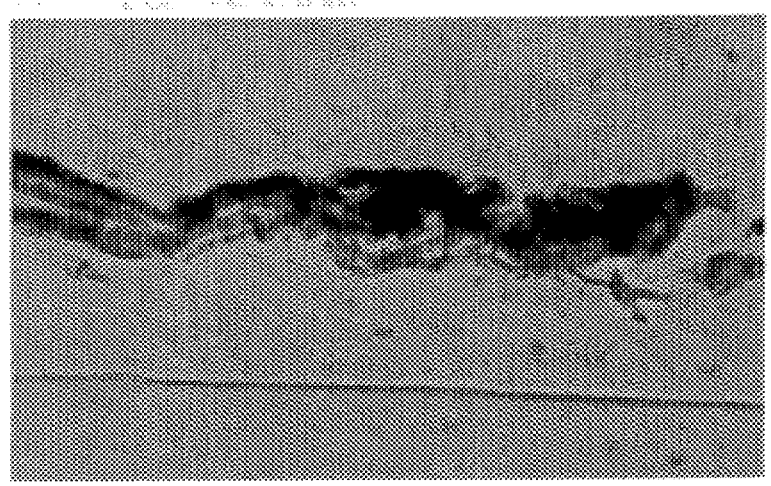
Figure 9B:
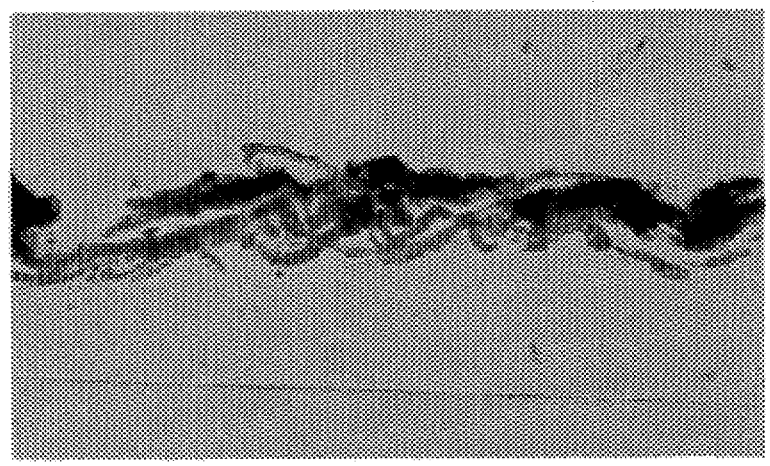
Figure 9C:
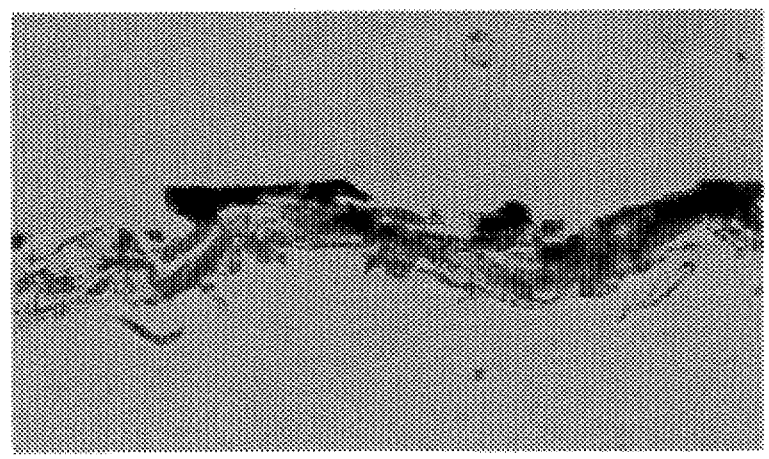
Figure 9D:
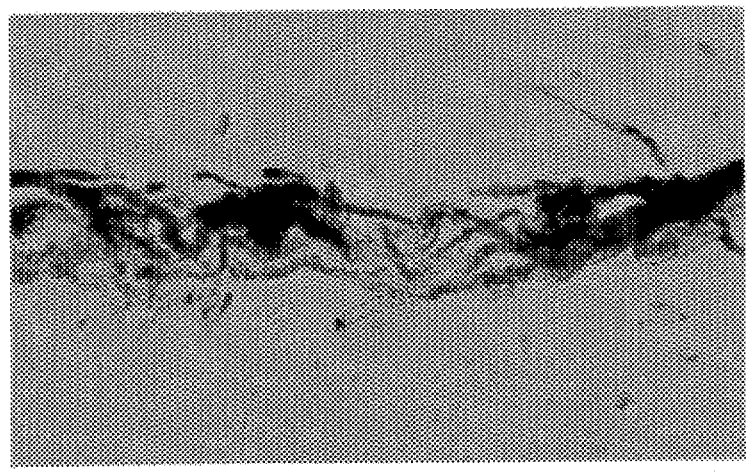
Figure 9E:
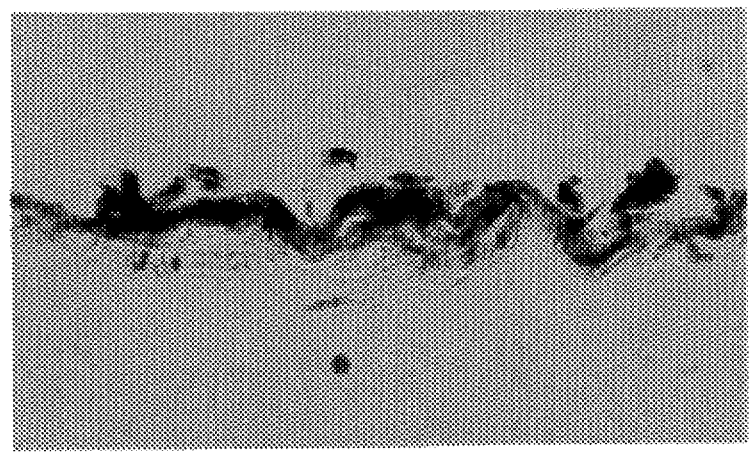
Figure 9F:
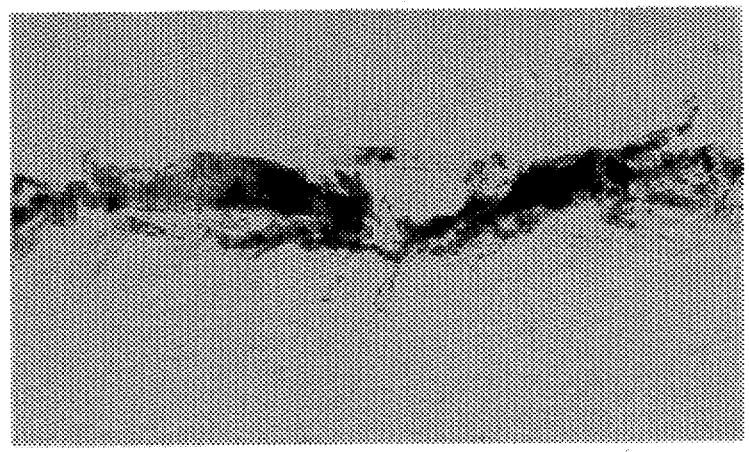
Figure 10A:
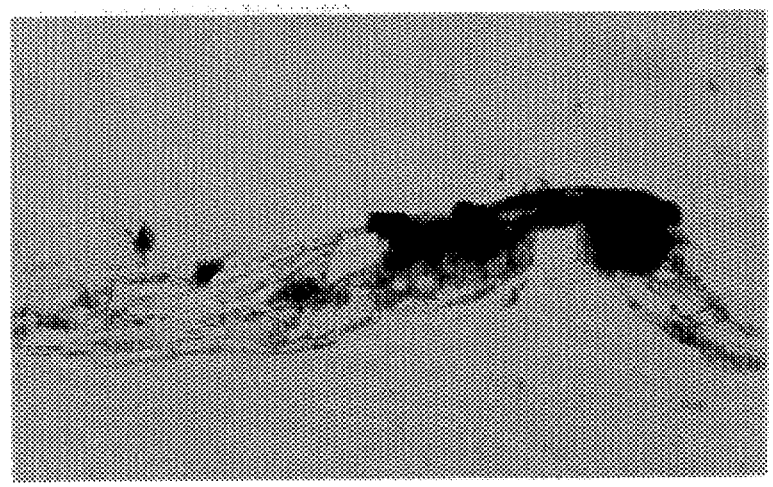
FIGS. 10A–F are cross-sectional photographs similar to those of FIGS. 8 and 9, but for a commercially available tissue product, PUFFS® Plus.
Figure 10B:
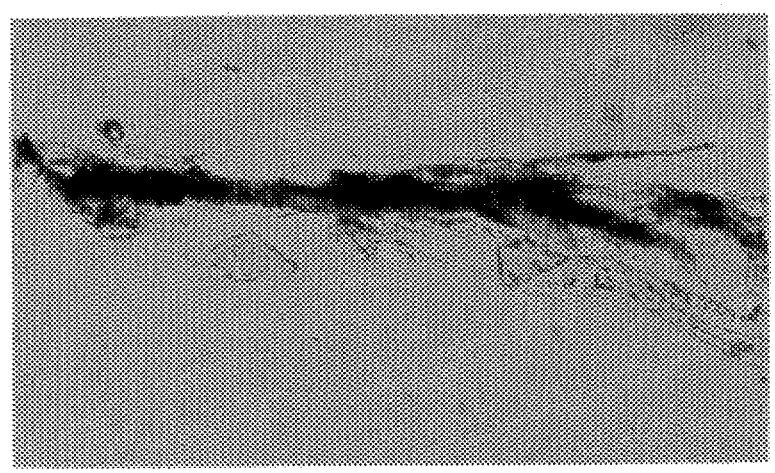
Figure 10C:
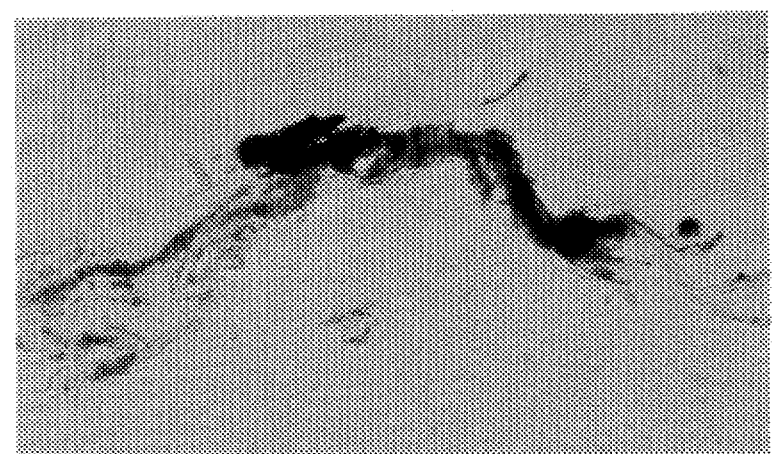
Figure 10D:
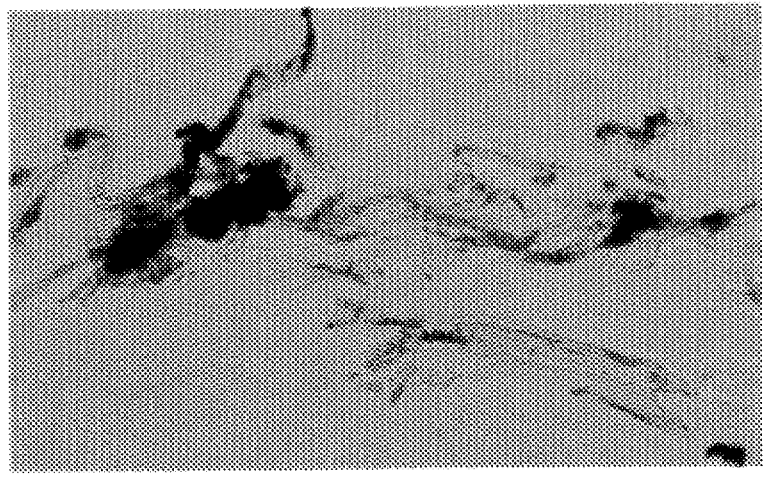
Figure 10E:
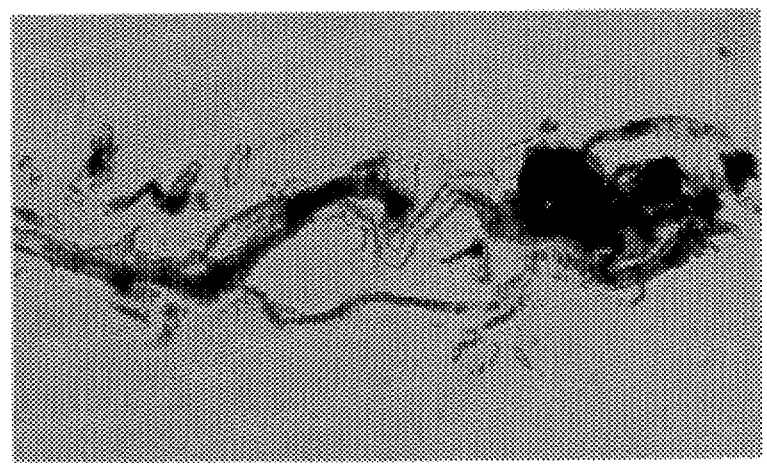
Figure 10F:
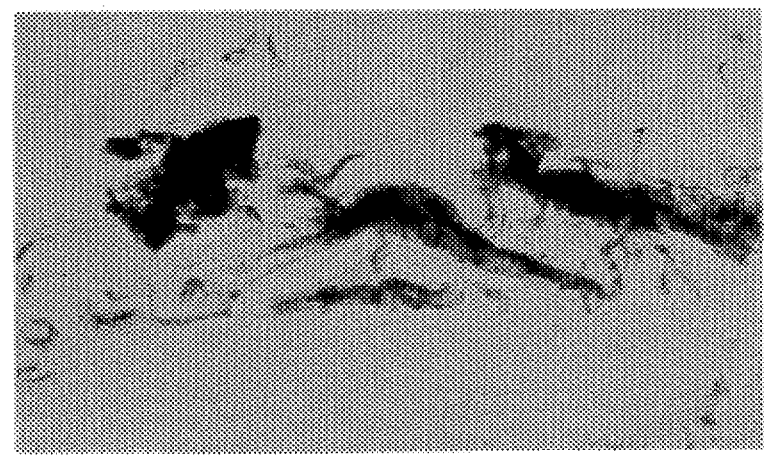

FIGS. 7A and 7B are plan views of the surface of a three-ply facial tissue of this invention (7A) and PUFFS® Plus facial tissue (7B), which is a commercially available lotion-treated tissue. The two tissues were treated with osmium tetroxide ($OsO_4$) vapors to render the translucent/white lotion visible against the white pulp fibers in the tissue. Osmium tetroxide reacts with available carbon double bonds to form osmium metal complexes with the carbon. This both stabilizes or "fixes" the affected material and stains the material black, which is desirable for generating contrast.

The osmium tetroxide treatment is carried out by placing the tissues loosely in a glass bell jar having an opening diameter of about 12–16 inches and a depth of about 12 inches. Care is taken not to stack the tissues, which would hinder adequate penetration of the vapors to all tissues. Osmium tetroxide is received as a crystalline solid in a sealed glass ampule which is broken open and placed in the bell jar with the tissues. The top is placed on the bell jar forming an air-tight seal. The tissues remain in the bell jar for about 24 to 48 hours. The osmium tetroxide has a high vapor pressure and sublimes readily to a gas which permeates the bell jar chamber. After staining is complete, the bell jar is opened and the samples are allowed to ventilate 12 to 24 hours before handling in order to release any residual unreacted vapors. Note: The greatest care must be exercised when using osmium tetroxide. It is a powerful oxidizer and highly toxic. All procedures with this material should be conducted in a fume hood with adequate air flow.

After the osmium tetroxide treatment, the tissues were viewed under a microscope at magnification of 7.5× with crossed-polarized light. As shown, the tissue of this invention exhibited greater uniformity in coverage. The uniformity was also confirmed using gray-level histogram analysis on the dyed tissues. The tissue of this invention had an average percent coefficient of variation (COV) of 10.6, whereas the PUFFS® Plus tissue had an average percent coefficient of variation of 22.6, indicating significantly less variability in coverage for the tissue of this invention.

In order to measure the percent coefficient of variation, the osmium-treated sheet was viewed with an omnidirectional darkfield lighting produced by an 8-bulb octagonal ring illuminator surrounding a 50 millimeter EL-Nikkor lens attached to a 10 millimeter C-mount extension tube. This was input into a Quantimet 970 Image Analysis System (Leica, Deerfield, Ill.) by a chainicon scanner. The field size (standard live frame) was 2.77 centimeters×2.17 centimeters. Various fields of the osmium-treated tissue were placed under the lens and measured using a black photodrape background. Six (6) fields in total were measured. The scanner white level is always set at 1.00 volt. At the end, the histogram was printed out and its standard deviation divided by its mean gray level to produce the coefficient of variation. When multiplied by 100, this becomes the percent coefficient of variation.

Referring to FIGS. 8 and 9 (this invention) and FIG. 10 (PUFFS® Plus), the three osmium tetroxide-stained tissues were cross-sectioned in the machine direction. Six representative segments (A–F) of each tissue were photographed under approximately 200× magnification to illustrate the difference in the degree of penetration of the composition deposits and the ability of the method of this invention to substantially confine the treatment composition to the surface of the treated tissue sheet. As shown, the PUFFS®Plus cross-sections illustrate that the treatment was sporadic and not uniform and more often penetrated completely through the tissue. By comparison, the tissues of this invention retained more of the treatment composition on the top surface of the treated ply.

The ability of the method of this invention to substantially retain the composition on the surface of the tissue was quantified using image analysis. More specifically, the imaging and optical conditions for this analysis were the same as described above for the uniformity measurement. But in this case, top surface and bottom surface pieces of each ply of tissue were placed tightly next to each other to form a "butt joint" with no gap between the two pieces. The sample is placed under the lens with, for example, the lighter bottom surface piece on the right of the image frame and the darker top surface piece on the left of the image frame.

If first measuring the gray-level histogram of the lighter, bottom surface, the variable live frame is placed over just that region of the image frame, with the scanner white level set at 1.00 volt for the whole field. Then the sample is rotated so that the lighter bottom surface is now on the left. The scanner is adjusted again to 1.00 volt and this surface is once again isolated by the variable live frame. This data is accumulated into the same gray-level histogram. The mean gray level for the bottom surface, $GL_{BOTTOM}$, is recorded.

The same procedure is then conducted on the darker, top surface that occupies the other half of the image, again with the scanner white level set at 1.00 volt for the entire image. (This will tend to compensate for the overall differences in the amount of the composition added to the tissue, while zeroing in more accurately on whether the composition is on the top or bottom surface, which reflects the degree of penetration.) Again, the mean gray level for the top surface, $GL_{TOP}$, is recorded.

Finally, the difference between the two mean gray levels, $GL_{DIFF}$, is calculated as a value inversely related to the penetration:

$$GL_{DIFF}=GL_{BOTTOM}-GL_{TOP}$$

Note that if $GL_{DIFF}$ is zero or negative, then complete penetration has occurred. If $GL_{DIFF}$ is strongly positive, then most of the osmium-stained composition is sitting on the top surface of the tissue.

The $GL_{DIFF}$ values for the two tissue samples of this invention as illustrated in FIGS. 8 and 9 were 10.4 and 6.1. By comparison, the PUFFS Plus tissue sample had a $GL_{DIFF}$ value of −2.1. In general, the tissues of this invention can be characterized by a $GL_{DIFF}$ of about 5 or greater, more specifically about 10 or greater, and still more specifically from about 5 to about 15.

EXAMPLES

Example 1

A skin-moisturizing formula having a melting point about 45° C. was prepared having the following composition:

|   | Weight Percent |
| --- | --- |
| 1. Dimethicone 100 cst | 1.0 |
| 2. Isopropyl Palmitate | 3.0 |
| 3. Vitamin E Acetate | 0.1 |
| 4. Aloe Extract | 0.1 |
| 5. Mineral Oil | 59.8 |
| 6. Ceresin Wax (M.P. 66–71° C.) | 18.0 |
| 7. Cetearyl Alcohol | 18.0 |

The formulation was prepared by premixing the dimethicone and the isopropyl palmitate until uniform. While heating, the aloe vera extract and the vitamin E extract were added and mixed. Mineral oil was added and the formulation was mixed until uniform. The mixture was further heated to a temperature of 55°–60° C. The ceresin wax was added. The mixture was further heated to 60°–65° C. with agitation until the ceresin wax was melted. Cetearyl alcohol was slowly added to the mixture while maintaining agitation to avoid clumping. The temperature was maintained at about 55°–60° C. and mixing continued until the cetearyl alcohol was melted. At this point the formulation was ready for use.

The resulting formulation was applied to both surfaces of a wet-pressed three-ply tissue basesheet (basis weight of about 23 pounds per 2880 square feet) via a heated rotogravure printing process at an add-on level of 16 weight percent total add-on as described in FIG. 4. Specifically, the formulation was pre-melted at about 56° C. in a stainless steel heated supply tank. The press supply system and press (supply hoses, doctor application heads, and gravure rolls) were preheated to about 55° C. The formulation was transferred from the heated application heads to the heated direct and offset gravure rolls.

The gravure rolls were electronically engraved, chrome over copper rolls supplied by Southern Graphics Systems, Louisville, Ky. The direct gravure roll had a line screen of 200 cells per lineal inch and a volume of 6.0 BCM per square inch of roll surface. Typical cell dimensions for this roll were 180 microns in length, 145 microns in width, and 34 microns in depth. The offset gravure roll was 250 line screen, 5.0 BCM, 150 microns in length, 110 microns in width and 30 microns in depth. The rubber backing roll/ offset applicator roll was a 72 Shore A durometer Flex Touch 1 supplied by Republic Roller, Three Rivers, Mich.

The direct gravure roll was set up to a condition having about 0.003 inch clearance from the rubber backing roll. The offset gravure roll was set up to a condition having 0.375 inch interference between the gravure roll and the rubber backing roll. The combination heated direct and heated offset gravure printer was run at a speed of 750 feet per minute. The composition deposits solidified substantially instantaneously after exiting the press.

When cut into individual facial tissue sheets, the resulting tissue product was preferred by consumers for softness, thickness, absorbency and overall over PUFFS Plus facial tissue.

Example 2

A skin-protecting formulation having the following composition and a melting point of about 56°–60° C. was prepared similarly to that of Example 1:

|   | Weight Percent |
| --- | --- |
| 1. Mineral Oil | 59.0 |
| 2. Zinc Oxide | 1.0 |
| 3. Ceresin Wax (M.P. 64–67° C.) | 20.0 |
| 4. Cetearyl Alcohol | 20.0 |

The above formulation was applied as described above to both surfaces of a one-ply uncreped throughdried bath tissue in an amount of 15 weight percent. The resulting tissue had an improved soft feel and was preferred overall over Charmin® Plus bathroom tissue.

Example 3

A skin moisturizing/protecting formulation with a melting point of about 61° C. having the following composition was prepared similarly to that of Example 1:

|   | Weight Percent |
| --- | --- |
| 1. Dimethicone | 2.0 |
| 2. Isopropyl Palmitate | 4.0 |
| 3. Acetulan* | 5.0 |
| 4. Mineral Oil | 45.0 |
| 5. Vitamin E Acetate | 2.0 |
| 6. Aloe Extract | 2.0 |
| 7. Ceresin Wax (M.P. 66–71° C.) | 20.0 |
| 8. Behenyl Alcohol | 20.0 |

*Cetyl acetate and acetylated lanolin alcohol, Amerchol Corp.

The above formulation was applied as in Example 1 to both sides of a two-ply facial tissue at a level of 26 weight percent total add-on.

Example 4

A three-ply facial tissue was prepared as described in Example 3, except the formulation add-on was 18 weight percent based on the weight of the two outer plies.

Example 5

A facial tissue was prepared as described in Example 4 except the add-on level was 22 weight percent based on the weight of the two outer plies.

In a consumer use test, the tissues of Examples 3, 4 and 5 were all preferred for softness, thickness, absorbency and overall over PUFFS® Plus.

Example 6

For comparison, treated tissues were prepared as described above with formulations which did not deliver a consumer-preferred product. Specifically, a first formula was prepared with the following ingredients:

|  | Weight Percent |
|---|---|
| 1. Dimethicone and Dimethiconal | 5.0 |
| 2. Dimethicone 20 cst | 15.0 |
| 3. Isopropyl Palmitate | 3.0 |
| 4. Isodecyl Neopentoate | 20.0 |
| 5. Acetulan | 7.0 |
| 6. Mineral Oil | 25.0 |
| 7. Glyceryl Monohydroxystearate | 15.0 |
| 8. Cetyl Alcohol | 10.0 |

This formulation was applied to a two-ply facial tissue as described above with a 14 weight percent total add-on level.

A second formulation was prepared with the following ingredients:

|  | Weight Percent |
|---|---|
| 1. Dimethicone 100 cst | 2.0 |
| 2. Isopropyl Palmitate | 4.0 |
| 3. Acetulan | 5.0 |
| 4. Mineral Oil | 34.0 |
| 5. Ceteareth-20 | 35.0 |
| 6. Cetyl Alcohol | 20.0 |

The second formulation was applied to a two-ply tissue at a total add-on level of about 31 weight percent.

Both products were submitted to a consumer use test for a preference comparison relative to PUFFS™ Plus (the Control) as was done with the products of Examples 3, 4 and 5. In both instances, PUFFS Plus was preferred. Both test formulas lacked a wax component (as selected from the list described earlier). It is believed that the lack of a wax component reduced the ability of the oil component to remain at or near the surface of the tissue and thus preventing a preferred result.

It will be appreciated that the foregoing examples, given for purposes of illustration, are not to be construed as limiting the scope of this invention, which is defined by the following claims and all equivalents thereto.

We claim:

1. A method of making a soft tissue product comprising:
   a) heating a composition comprising an oil and a wax to a temperature above the melting point of the composition, causing said composition to melt, said composition having a melting point of from about 30° C. to about 70° C.;
   b) uniformly applying the melted composition to one or both surfaces of a tissue web in spaced-apart deposits; and
   c) resolidifying the deposits of the melted composition.

2. The method of claim 1 wherein the heated composition is applied to the tissue web with a rotogravure printer providing from about 100 to about 1,000,000 deposits per square inch.

3. The method of claim 2 wherein from about 30 to about 99 percent of the surface area of the tissue is covered with the composition.

4. The method of claim 2 wherein from about 50 to about 80 percent of the surface area of the tissue is covered with the composition.

5. The method of claim 1 wherein the amount of the composition applied to the tissue is from about 1 to about 40 weight percent.

6. The method of claim 1 wherein the amount of the composition applied to the tissue is from about 5 to about 25 weight percent.

7. The method of claim 1 wherein the amount of the composition applied to the tissue is from about 10 to about 15 weight percent.

8. The method of claim 1 wherein the tissue web is cooled before or after the deposits of the coating composition are applied in order to accelerate solidification of the deposits.

9. The method of claim 1 wherein the composition is heated to a temperature of about 10° C. or less above the melting point of the composition.

10. The method of claim 1 wherein the composition is heated to a temperature of about 5° C. or less above the melting point of the composition.

11. The method of claim 1 wherein the composition is heated to a temperature of about 2° C. above the melting point of the composition.

12. The method of claim 1 wherein the composition contains from about 5 to about 40 weight percent fatty alcohol.

13. The method of claim 1 wherein the tissue is a facial tissue.

14. A method of making a soft tissue sheet comprising:
   (a) heating a composition comprising an oil and a wax to a temperature above the melting point of the composition, causing the composition to melt, said composition having a melting point of from about 30° C. to about 70° C.;
   (b) continuously uniformly applying the melted composition to one side of a tissue web in spaced-apart deposits;
   (c) resolidifying the deposits of the melted composition; and
   (d) winding the resulting tissue into a roll.

15. A method of making a soft tissue sheet comprising:
   (a) heating a composition comprising an oil and a wax to a temperature above the melting point of the composition, causing the composition to melt, said composition having a melting point of from about 30° C. to about 70° C.;
   (b) continuously uniformly applying the melted composition to both sides of a tissue web in spaced-apart deposits;
   (c) resolidifying the deposits of the melted composition; and
   (d) winding the resulting tissue into a roll.

* * * * *